United States Patent [19]

Gangarosa et al.

[11] Patent Number: 4,835,690
[45] Date of Patent: May 30, 1989

[54] INTEGRATED EXPERT SYSTEM FOR MEDICAL IMAGING SCAN, SET-UP, AND SCHEDULING

[75] Inventors: Raymond E. Gangarosa, Euclid, Ohio; Edward A. Patrick, W. Lafayette; James M. Fattu, Evansville, both of Ind.; Andrew S. Green, Bedford, Ohio

[73] Assignee: Picker International, Inc., Highland Heights, Ohio

[21] Appl. No.: 181,116

[22] Filed: Apr. 13, 1988

Related U.S. Application Data

[63] Continuation of Ser. No. 799,427, Nov. 19, 1985, abandoned.

[51] Int. Cl.⁴ .............................................. G06F 15/42
[52] U.S. Cl. ............................ 364/413.13; 364/513; 364/300
[58] Field of Search ............... 364/148, 149, 152, 178, 364/442, 431.02, 431.04, 414, 513, 300; 324/309, 307, 312; 324/309, 307, 312

[56] References Cited

U.S. PATENT DOCUMENTS

| | | | |
|---|---|---|---|
| 4,368,509 | 1/1983 | Li | 364/148 |
| 4,620,153 | 10/1986 | Hino | 364/414 |
| 4,633,403 | 12/1986 | Asmu | 364/431.05 |
| 4,639,870 | 1/1987 | Otake | 364/431.05 |
| 4,658,370 | 4/1987 | Erman | 364/513 |
| 4,661,909 | 4/1987 | Kumazawa | 364/414 |
| 4,670,848 | 6/1987 | Schramm | 364/513 |

OTHER PUBLICATIONS

"Nuclear Magnetic Resonance: A Gray Scale Model for Head Images" by Droege, et al., Radiology, 148, Sep. 1983, pp. 763–771.

"Signal, Noise, and Contrast in Nuclear Magnetic Resonance (NMR) Imaging" by Edelstein, et al., Journal of Computer Assisted Tomography, Jun. 1983, pp. 391–401.

"Parameters Determining the Appearance of NMR Images" by Wehrli, et al; Modern Neuroradiology, vol. 2, 1983.

"Normal and Abnormal Anatomy of the Head: Dependence on Imaging Technique and Parameters" by Mills, et al., Program and book of abstract, Boston, pp. 107–108 (Aug. 1982).

(List continued on next page.)

*Primary Examiner*—Michael R. Fleming
*Attorney, Agent, or Firm*—Fay, Sharpe, Beall, Fagan, Minnich & McKee

[57] ABSTRACT

A magnetic resonance or other diagnostic imaging scanner (A) is connected with an image reconstruction module (B) for reconstructing diagnostic images. An integrated expert system (C) selects scan parameter settings for conducting the scan such that utility of the image is optimized for the intended diagnosis. A keyboard (12) receives subject and intended diagnostic application data such as the age of the patient, the region of the patient to be imaged, the anticipated size of the lesion, and the like. A first expert system (10) derives appropriate constraints on values for each performance index and priorities for each performance index from the subject and intended application data. The performance indices include contrast, resolution, scan suration, and the like. A scan parameter estimator look-up table (14) is addressed by the performance index constraints and priorities and retrieves corresponding estimated scan parameters. A second expert system (16) adjusts the estimated scan parameter settings to optimize a performance function (26). That is, the performance index values are predicted by a preselected mathematical model which relates scan parameters and performance indices. The scan parameters settings are adjusted until the predicted performance indices have an optimal fit with preselected ideal performance index values with higher priority performance indices being weighted more heavily than lower priority indices and with the predicted performance values being within the constraints.

22 Claims, 6 Drawing Sheets

OTHER PUBLICATIONS

"Calculated NMR Images" by Ortendahl, et al., Presented at 2nd Annual Meeting of the Society of Magnetic Resonance in Medicine, San Francisco, Aug. 1983.

"Imaging Principles in Computed Tomography" by F. Miraldi, about 1983.

"Statistical Analysis of NMR Spin–Lattice Relaxation Times" by T. K. Leipert and D. W. Marquardt, Journal of Magnetic Resonance, 24, 1976, pp. 181–199.

"An Iterative Linear Method for Calculation of Spin–Lattice Relaxation Times", by Crouch, et al., Journal of Magnetic Resonance, 1976, pp. 371–382.

"Visualization of Cerebral and Vascular Abnormalities by NMR Imaging, The Effects of Imaging Parameters on Contrast" by Crooks, et al., Radiology, 144, Sep. 1982, pp. 843–852.

"Automated MR Image Synthesis: Feasibility Studies" by Riederer, et al., Radiology, 1984, 153: pp. 203–206.

"A Strategy for Magnetic Resonance Imaging of the Head: Results of a Semi-Emprical Model" by Droege, et al. Radiology, 1984; 153; pp. 419–424.

"Generalized Image Combinations in Dual KVP Digital Radiography" by Lehmann, Med. Phys. Sep./Oct. 1981, pp. 659–667.

Radiological Imaging, Chapter 4, Barrett, et al., Academic Press, NY, 1931, pp. 117–191.

"Scientific Program", Radiology, 1983, pp. 278 and 97 vol. 149.

"Two Computer Models for Selection of Optimal Magnetic Resonance Imaging Pulse Sequence Timing" by Mitchell, et al. Investigative Radiology, Sep.–Oct. 1984, vol. 19, No 5, pp. 350–360.

"Concepts of an Estimation System, an Adaptive System, and a Network of Adaptive Estimation Systems" by Edward Patrick, IEEE Transactions on Systems Science and Cybernetics, vol. SSC-5, No 1, Jan. 1969, pp. 79–85.

"Artificial Intelligence Gives Computer New Role as Imaging Problem Solver" by Ezquerra, et al., *Diagnostic Imaging*, Nov. 1985, pp. 195–200.

INTEGRATED EXPERT SYSTEM FOR MEDICAL IMAGING SCAN, SET-UP, AND SCHEDULING

This application is a continuation of application Ser. No. 799,427, filed Nov. 19, 1985, to Raymond E. Gangarosa, et al., entitled "Integrated Expert System for Medical Imaging Scan, Set-up, and Scheduling" now abandoned.

BACKGROUND OF THE INVENTION

The present invention relates to the art of operating parameter optimization. It finds particular application in conjunction with optimizing scan parameters for a magnetic resonance imaging apparatus and will be described with particular reference thereto. It is to be appreciated, however, that the present invention is also applicable to the otpimization of scan parameters in conjunction with computerized tomographic scanning apparatus, magnetic resonance spectrometers, other non-invasive medical imaging and diagnostic apparatus, and the like.

Heretofore, the operating parameters of magnetic resonance imaging apparatus has commonly been set based on the experience of the operator. These operating parameters included selection of the imaging sequence, scan times, slice thickness, number of views to be summed in each image, and numerous other operating parameters as are conventional in the art. As might be expected, the suitability of a resultant image for the intended diagnostic purposes varied widely from operator to operator.

Operator educational systems helped the operator to understand the significance of various operating parameters. The education helped to obtain greater consistency of results from operator to operator. One such education system incorporated image simulation by mathematical modeling of individual ones of the performance indices, such as contrast, signal-to-noise, and, motion rejection. From this simulation, the operator came to understand more precisely the effect on the ultimate image that various adjustments of the twenty or so scan parameters on the intitial protocol would achieve.

Another educational tool involved a retrospective image synthezization. Three scans were taken through the same slice or region of a patient, each with different scan parameters. In one scan, the scan parameters were set to emphasize proton density; in the second scan, the scan parameters were set to emphasize T1 relaxation time; and, in the third scan, the parameters were set to emphasize T2 relaxation time. The images from these three scans were electronically mixed with different weightings to illustrate the effects of adjustments to the various available scan parameters. The differently weighted electronically mixed images each emphasized or obscured different lesions, tumors, tissues, disease processes, and the like to different degrees. In this manner, the operator was trained to select the most characteristic scan parameters for the medical diagnostic purpose at hand. This retrospective system had the drawbacks of relying on operator skill. Moreover, the educational techniques tended to focus on a single scan parameter without educating the operator on how the various scan parameters interacted synergistically to affect the final image.

In another retrospective technique, three images were taken of the scan plane of a patient being diagnosed, each image emphasizing one of proton density, T1 relaxation time, and T2 relaxation time. After the scanning was complete and the patient had left, the three images were mixed with various weightings. The various mixings attempted to optimize a performance variable or otherwise optimize the characteristics of the resultant image for the selected diagnosis. This technique was again inefficient. Extra scanning time was required to collect the multiple scans. Further, the flexibility was limited to modifying the image reconstruction with previously collected data. The three images were each taken with a different but fixed protocol of scan parameters, none of which were commonly optimal for the diagnosis in question.

The prior art suffers from several drawbacks including an inability to individualize the examination to a patient being imaged. Rather, it must rely on historical data or learning. Another drawback is a relative inflexibility in the potential combinations of scan parameters. Commonly, machine adjustability is limited in order to achieve simplicity of operation. Further, operators are rarely capable of appreciating the full significance of adjustments to the twenty or so scan parameters that might be adjusted.

The present invention provides a new and improved automatic optimization of all scan parameters for the nature of the diagnosis to be performed with the resultant image.

SUMMARY OF THE INVENTION

In accordance with one aspect of the present invention, a non-invasive medical imaging system is provided. A non-invasive examination means, e.g. a magnetic resonance excitation apparatus, selectively examines a subject and derives electrical signals indicative of a monitored property thereof. The examination means has a plurality of adjustable scan parameters. An image reconstruction means derives an image indicative of the monitored property of the examined subject. The image is described by a plurality of performance indices which are related to the scan parameters by a preselected mathematical model. Although each performance index has a preselected ideal value, the ideal values for all performance indices cannot be attained simultaneously. A performance index means selects relative priorities for optimizing each performance index based on received clinical information on the subject and the intended diagnostic application for the image. An optimizing means optimizes the performance index values in accordance with the relative priorities. At optimization, the corresponding scan parameter settings are supplied to the examination means.

In accordance with another aspect of the invention, an operating parameter selection system is provided. An input means receives intended application data. A first system derives constraints on values for each of a plurality of performance indices and a weighting factor or priority for each performance index. A second system derives operating parameter settings from the performance index constraints and priorities.

In accordance with a more limited aspect of the invention, the performance indices and the parameters are interrelated such that adjustments in one operating parameter setting affects more than one of the performance indices values. The second expert system selects the operating parameter settings which optimize overall performance. Specifically, the second expert system adjusts the operating parameter settings until the higher priority performance indices are optimized while maintaining substantially all performance index values within the constraints.

In accordance with another aspect of the the present invention, a parameter estimator means estimates optimal operating parameter settings for the intended application. The second expert system selectively alters the estimated operating parameter settings from the parameter estimator means to optimize the output data for its intended use. In particular, the operating parameters are adjusted until a performance functional of the constraints and priorities is optimized. In this manner, the estimator means reduces the complexity of the optimization tasks of the second expert system.

In accordance with another aspect of the present invention, patient scheduling is optimized by an integrated expert system. Scheduling considerations for each patient are assigned a constraint and relative priority by a first expert system. Potential patient schedules are iteratively adjusted by a second expert system until an optimal patient schedule is derived.

One advantage of the present invention resides in selecting the scan parameters prior to commencement of each scan to optimize utility of a generated image or other information for its intended use.

Another advantage of the present invention is that it permits variations of a large number of scan parameters. A larger number of scan parameters than can normally be considered by a human operator are rapidly considered and evaluated.

A further advantage is that the user can constrain or assign priorities to selected performance indices to direct the optimization process. This adapts the system to a wide range of user experience and applications rendering it useful for both novice operators and those with considerable experience.

Yet another advantage of the present invention is an optimization of scheduling and diagnostic apparatus utilization.

Still further advantages will become readily apparent to those of ordinary skill in the art upon reading and understanding the following detailed description of the preferred embodiments.

BRIEF DESCRIPTION OF THE DRAWINGS

The invention may take form in various components and arrangements of components or in various steps and arrangements of steps. The drawings are only for purposes of illustrating a preferred embodiment of the invention and are not to be construed as limiting it.

DETAILED DESCRIPTION OF THE PREFERRED EMBODIMENTS

Figure 1:
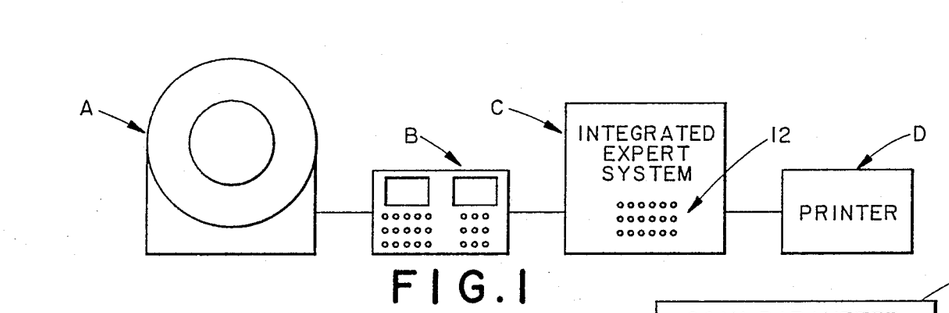
FIG. 1 is a diagrammatic illustration of a magnetic resonance imaging system in accordance with the present invention.

With reference to FIG. 1, a magnetic resonance scanner A selectively excites magnetic resonance in selected dipoles of a subject to be imaged and receives magnetic resonance signals from the resonating dipoles. The magnetic resonance means has several, in the preferred embodiment, about twenty adjustable scan or operating parameters including scan sequence, repeat time, number of views, number of acquisitions, number of slices, echo time, slice thickness, field of view, and the like. By selecting different combinations of scan parameters, various features may be emphasized in the received resonance signals and a resultant image. Magnetic resonance spectrometers, C.T. scanners, other medical imagers, and other associated appartus are also contemplated by the present invention.

A display means B, in the preferred embodiment an image reconstruction means, displays information derived from the electrical signals of the scanner A. More specifically to the preferred embodiment, the means B reconstructs and displays an image from the magnetic resonance signals.

Various performance indices of the displayed images are affected by the selected scan parameter settings. The performance indices are selected variables each of which has a definitely measurable result or interpretation on the reconstructed image or other displayed output data. With the preferred magnetic resonance imaging apparatus, the performance indices include contrast, signal-to-noise ratio, resolution, slice thickness, field of view, motion rejection, time, and survey length. Each selected scan parameter commonly affects more than one of the performance indices. Accordingly, each change in the selected scan parameter settings affects the characteristics of the resultant image, hence the value of one or more of the performance indices. As discussed above, these image characteristics might emphasize resonating dipole density, relaxation times, selected tissue configurations, and other properties of the subject to be imaged. When diagnosing various maladies and conditions, different lesions, tissue types, and conditions become emphasized with different scan parameters. The optimum image characteristics are thus a function of the intended diagnostic use of the image as well as the subject to be imaged.

An integrated expert system C derives scan parameter settings from received clinical information on the intended diagnostic application and subject which optimize the image or other output for the intended use. More specific to the preferred embodiment, the integrated expert system or other parameter selection means determines appropriate scan parameters for the subject and intended application. In the preferred embodiment, the scan parameter selection means adjusts the parameter settings until the performance indices values, hence the characteristics of the resultant image, are optimized for the intended use. The parameter selection means is operatively connected with the magnetic resonance scanner A and the image reconstruction means B to implement the selected scan parameter settings automatically. Optionally, the parameter selection means may be connected with a printer D or other display for displaying the optimum scan parameter settings. The displayed optimum scanned parameter settings are then manually programmed into the controls for the magnetic resonance scanner by the operator.

The parameter selection means C also schedules patients for the magnetic resonance scanner. Various scheduling criteria are entered, including information on the subjects, the urgency of the scan, the intended use of the scan, and the like. The integrated expert system or means not only optimizes the scan parameter settings for each scan, but also prioritizes the order in which the patient should be scanned, selects appropriate numbers of scans and scan durations for each patient in accordance with the intended diagnostic use of the images and the scheduling demands of the magnetic resonance scanner. An appropriate or optimized patient schedule is printed on the printer D or otherwise displayed.

Figure 2:
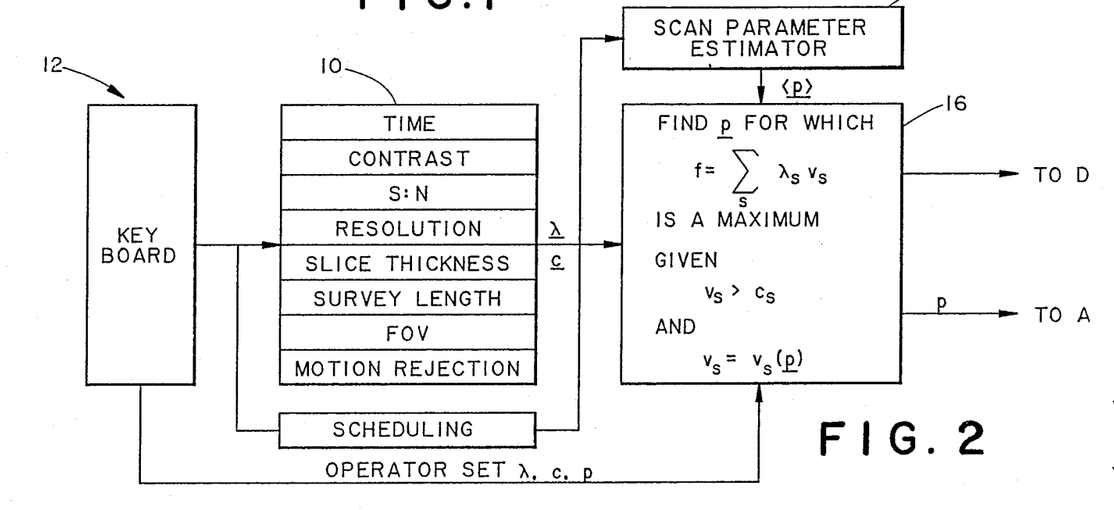
FIG. 2 is a diagrammatic illustration of the integrated expert system of FIG. 1.

With reference to FIG. 2, the integrated expert parameter selection system C includes a first or performance index expert system 10. The first expert system receives clinical descriptions, such as information on the patient, patient history, and diagnostic issues involved. From the clinical description, the first expert system 10 derives appropriate constraints on performance index values and priorities for each performance index. More specifically, each performance index has a preselected ideal value. However, there is no set of operating or scan parameters which will enable all the performance indices to attain their respective ideal values simultaneously. Rather, an overall optimal or best attainable degree of conformity with the preselected ideal values is obtained during optimization. The constraints or constraint values are indicative of a maximum acceptable deviation between the achieved and preselected ideal value for each performance index. The priorities or priority values each indicate the relative weight or importance of each performance index.

The first expert system 10 may obtain the performance index constraint and priority values using any one of several known techniques. In one embodiment, the first expert system includes a look-up table for looking up appropriate constraints and priorities in response to being addressed by the clinical descriptions, i.e. subject and intended use data, which is received. The clinical descriptions are received from an input means such as a keyboard 12. A conventional dispute resolution program or system resolves conflicts between performance index constraints and priorities which are retrieved in response to different ones of the clinical descriptions. For example, the performance indices which correspond to each clinical description may be prioritized to facilitate a determination of which clinical description will determine the constraints and priorities for each performance index.

In another embodiment, a mathematical optimization routine iteratively adjusts the constraint and priority values for each performance index until a best or optimal fit or confirmity is achieved.

The integrated expert system C also includes a parameter estimator means or expert system 14 for estimating scan or operating parameters based on the priority and constraint values. The parameter estimator may again be a look up table or other system which correlates the performance index constraint and priority values with the scan parameter settings.

A second or mathematical optimization expert system 16 receives the estimated parameter settings from the parameter estimator means 14, priority and constraint values from the first expert system 10, and any constraint values, priority values, or parameter settings which may be input by the operator on the keyboard 12.

The mathematical optimization system in the preferred embodiment iteratively adjusts the scan parameter settings until the performance indices, hence the utility of the resultant image for its intended diagnostic use, are optimized. More particularly, a performance functional, which is related to the priority of each performance index and the proximity of the achieved and preselected optimum performance index values, is optimized while holding all performance index values within the constraints.

Upon optimizing the performance functional, the scan parameter settings of the magnetic resonance scanner are automatically adjusted by the integrated expert system C. Optionally, the settings may be displayed on the printer D and the scanner set by the operator. If the performance functional cannot be optimized within the constraints, an appropriate message will be printed on the printer D or other display means. The operator may then manually adjust the constraints or priorities on the keyboard before the mathematical optimization process is repeated.

A scheduling means 18 schedules patient examinations for optimal utilization of the scanner and optimal patient service. In a simplest embodiment, the scheduling step or means B keeps track of how much time each patient needs and determines whether it falls within a pre-allotted time or time constraint. In the preferred embodiment, a relative weighting or priority and scheduling constraints are assigned for each patient. The scheduling priorities indicate how soon a scan needs to be done, the relative importance of the scans, the importance of doing a full rather than partial set of requested scans, and the like. The scheduling constraints place limits on the scheduling times. The mathematical optimizing means 16 generates an optimal patient schedule for the given constraints and priorities. The schedules are printed on the printer D to provide the patients scheduling for that day or other appropriate time period.

The expert systems may be look-up tables or probability based systems. Each system may implement Bayesian a priori probabilities, similar a priori probabilities and weights for a Bayesian decision theory, stored records which are used to obtain the Bayesian analysis of probabilities or weighted probabilities, production rules, a combinatorial approach to artificial intelligence, combinatorial searches, or the like.

Figure 3A:
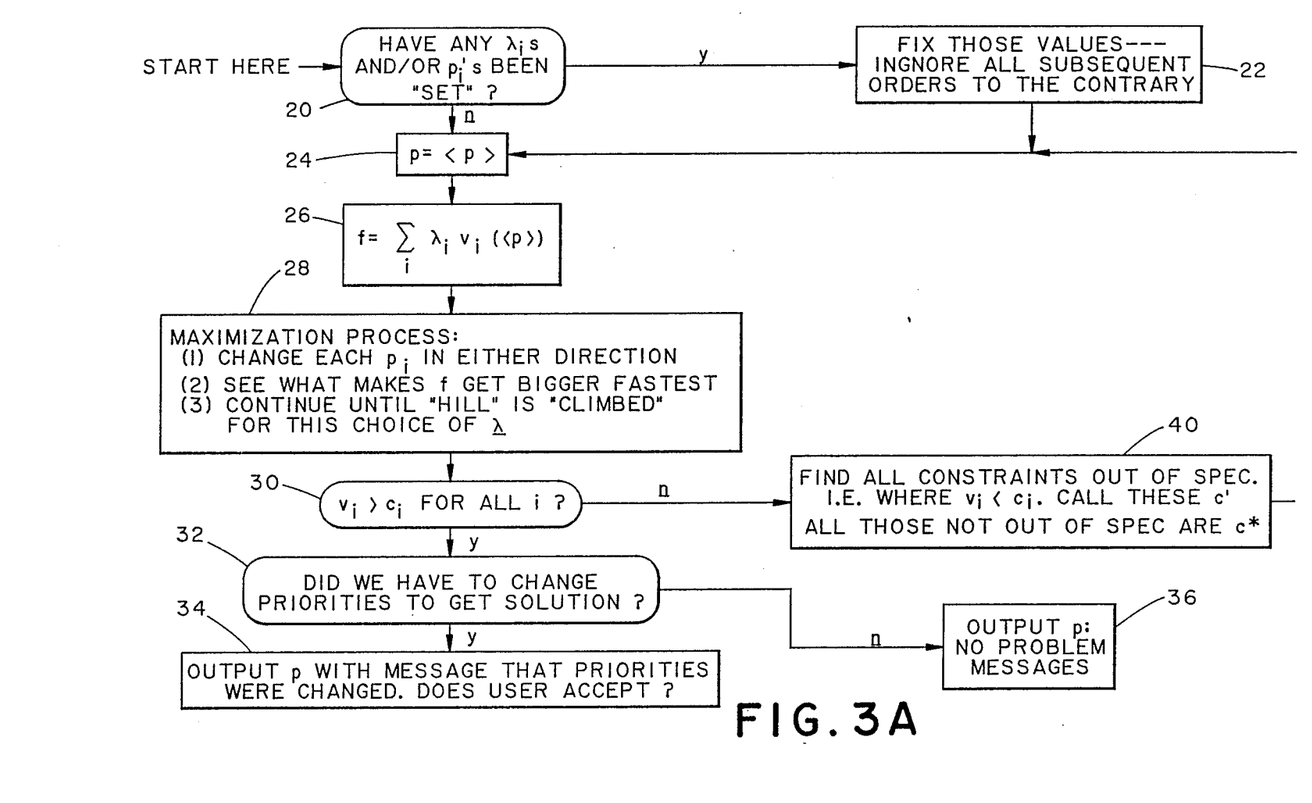
FIG. 3a and 3b are a programming flow chart which describes the logic operations to be performed by the mathematical optimization means of FIG. 2.
Figure 3B:
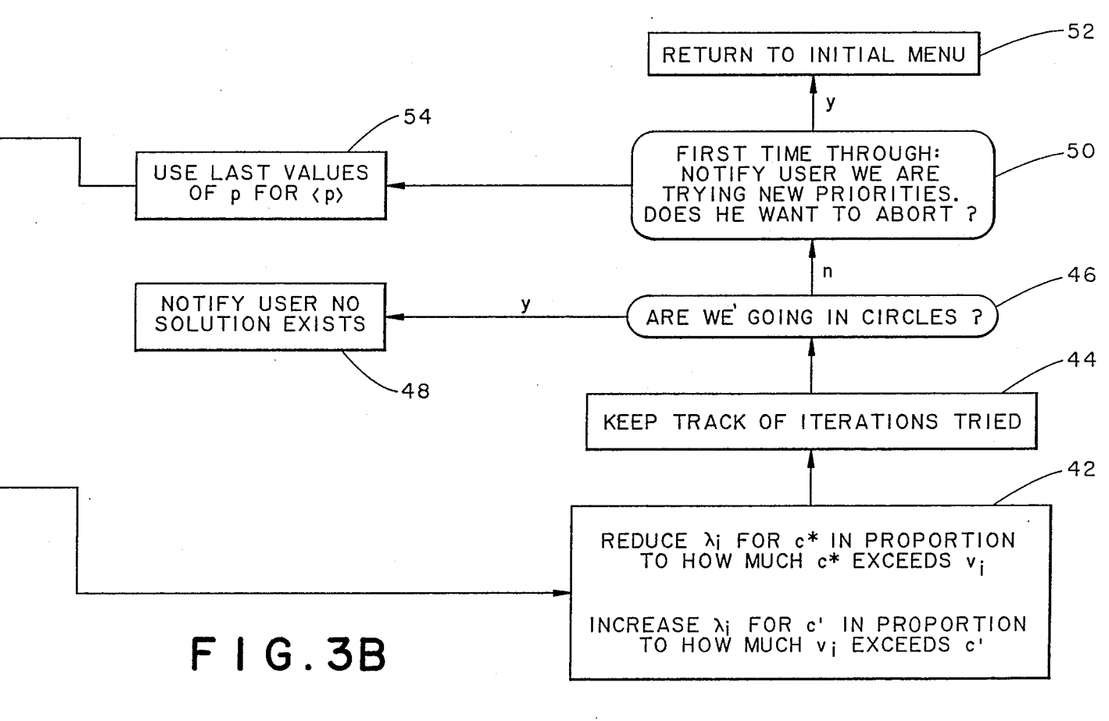

FIG. 3 illustrates a preferred on-line implementation of the mathematical optimization of the second expert system 16. In the on-line mathematical optimization, the possible combinations of scan parameter settings are analyzed and the performance function is optimized while a patient is in place. A step or means 20 determines whether any constraints, priorities, or scan parameter settings have been designated by the operator. If so, a step or means 22 fixes those values such that the optimization process does not alter any of the set constraints, priorities, or scan parameters. A step or means 24 retrieves estimated scan parameter settings from the parameter estimator 14. A performance functional step or means 26 implements an equation for a performance functional, f, which is to be optimized. The performance functional is a mathematical equation which relates the proximity of each performance index value as predicted from a mathematical model to the preselected optimum and the weighting of the corresponding priorities. In the preferred embodiment, a linear performance function is utilized:

$$f = \sum_i \lambda_i v_i(<p>) \tag{1}$$

where $\lambda_i$ is the priority of the ith performance index and $v_i$ is a mathematical model for predicting the difference between the preselected optimum performance index and a mathematically predicted performance index value. For the eight performance indices (1) time, (2) contrast, (3) signal-to-noise, (4) resolution, (5) slice selection, (6) survey length, (7) field of view, and (8) motion rejection, exemplary values of $v_i$ are:

$$v_1 = -k_1 T_t \tag{2a}$$
$$v_2 = v_2(T_R, T_E) = k_2 \Delta I = k_2 \{I(T_{1l}, T_{2l}) - I(T_{1b}, T_{2b})\} \tag{2b}$$
$$v_3 = k_3 S{:}N = k_3 G_{coil} F_v^2 N_p^{-\frac{1}{2}} T_i^{\frac{1}{2}} S_t^{\frac{1}{2}} \ \mu/m \tag{c}$$
$$v_4 = k_4 R = 0.5 k_4 N_y/F_v \tag{2d}$$
$$v_5 = -k_5 S_t \tag{2e}$$
$$v_6 = k_6 L_s = k_6 N_s S_t \tag{2f}$$
$$v_7 = -k_7 F_v \tag{2g}$$
$$v_8 = k_8 \ \mu/m, \tag{2h}$$

where
$T_t = T_i + T_{recon}, \ T_i = k T_r N_y N_2 Q \mu, \ k = 0.0000167,$
$T_{recon} = a_1(Q - 1) + a_2 Q N_s, \ a_1 = 2, \ a_2 = 0.167.$
$I = I(T_R, T_E, T_1, T_2) = e^{-TE/T2} \{1 + e^{-TR/T1} - 2e^{(TE/2 - TR)/T1}\}$ and subscripts l and b refer to lesion and background, respectively.

$T_t$ = total examination time,
$T_i$ = imaging time,
$T_{recon}$ = reconstruction time,
$G_{coil}$ = coil sensitivity factor.
$N_p$ = image matrix, $]\mu$ = empirically determined factor relating to motion artifact rejection (No movement rejection $\rightarrow \mu = 1$),
m = relative amount of movement present (No movement $\rightarrow$ m = 1), and
$k_i$ = positive scaling constant for each performance index $v_i$, i = 1, . . . , 8.

This linear performance function is given by way of example. Optionally, polynomial, quadiadic, absolute value, and the like performance functions may also be utilized.

A maximization means or step 28 incrementally adjusts each scan parameter settings until the performance functional is optimized. In the preferred embodiment, the performance functional is maximized. Each estimated scan parameter setting is adjusted incrementally in either direction to determine whether the performance functional increases. The scan parameter setting adjustment is continued until the performance functional is maximized. The scan parameters are cyclically adjusted until no movement in the performance functional can be achieved by changing any of the scan parameters.

Having optimized or maximized the performance functional, a step or means 30 determines whether all the constraints are met. If all the performance index values are within the constratins, then a step or means 32 checks to determine whether any performance index priorities had to be adjusted in the optimization. If any of the priorities were changed, a display generating means or step 34 generates an appropriate display to the operator. The operator may readjust the priorities and constraints and start the program again. If the operator is willing to accept the new priorities or if none of the priorities have been changed, then an output step or means 36 conveys the scan parameter settings to the magnetic resonance scanner to control the scans in accordance therewith.

If all the constraints to the performance indices were not met in the step or means 30, a step or means 40 determines which constraints are not met. A step or means 42 alters the performance index priorities in accordance with the deviation from the corresponding constraint.

An iteration monitoring means or step 44 monitors the iterations and an endles loop determining step or means 46 determines whether the program has entered an endless loop. If there is no solution optimization to the formulated problems, a display means or step 48 causes a display to notify the operator that no solution exists with the presently selected priorities and constraints. In this manner, the program does not change the constraints but only advises the operator that the selected constraints cannot be met, requesting that the operator select new constraints.

A step or means 50 notifies the operator if new priorities are being substituted for the originally selected priorities and asks the operator whether he wants to select new constraints rather than allowing the new priorities to be substituted. If the operator wants to change the priorities, a step or means 52 returns the operator to an initial menu where new priorities, constraints, and scan parameter settings may be selected. If the operator is willing to accept the new priorities, a step or means 54 loads the scan parameter settings into step or means 24 and another iteration through the loop is commenced.

Figure 4:
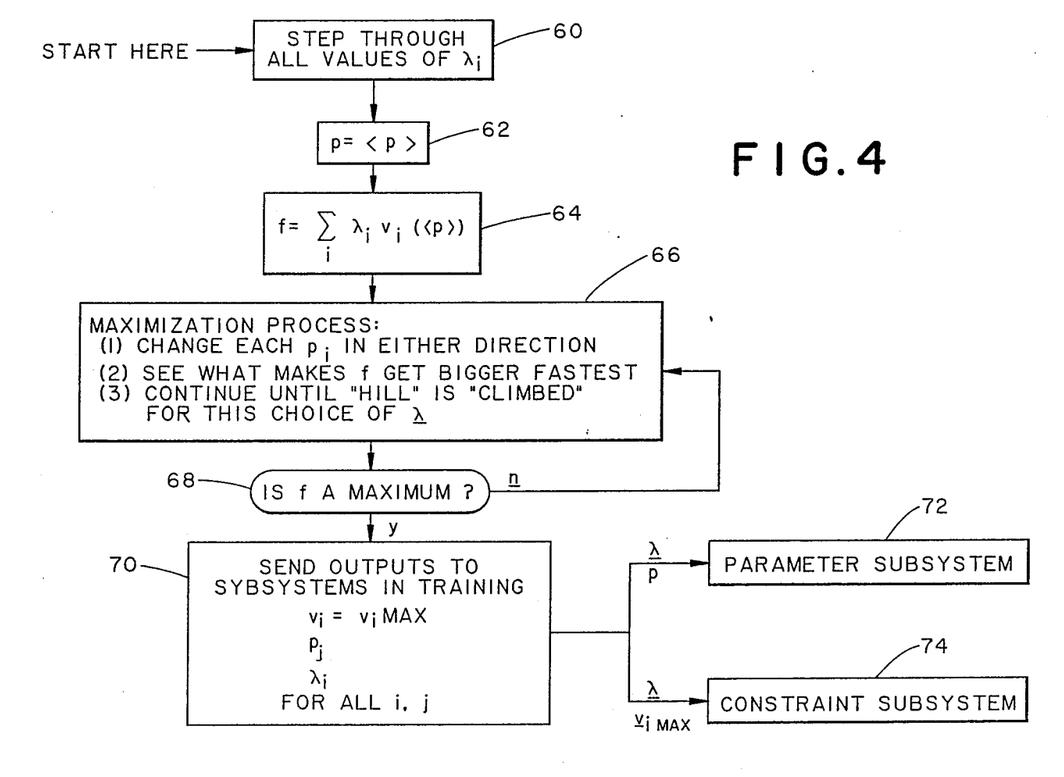
FIG. 4 is a system flow chart outlining the logic to be implemented for an off-line version of the mathematical optimization subsystem.

FIG. 4 illustrates an off-line mathematical optimization procedure. In the embodiment of FIG. 4, the best performance index constraint possible with each priority weighting value is determined for the potential scan parameter settings. The determined scan parameter settings are arranged in a look-up table or the like. The parameter estimator 14 of FIG. 2 is preferably a look-up table programmed in accordance therewith. A stepping or indexing means or step 60 steps through all possible values for the priorities of each of the eight performance indices. An initial scan parameter step or means 62 sets initial scan parameter settings for the optimization process. These may be manually entered by the operator, retrieved from a look-up table or the like.

A performance functional step or means 64 calculates the performance functional analogously to the on-line performance functional step or means 26 of FIG. 3. A maximizing step or means 66 maximizes or otherwise optimizes the performance functional analogous to step or means 28 of FIG. 3. A maximum determining means 68 determines whether the performance functional, f, has truly been optimized. If not, the program loops through the step or means 66. Once the performance functional has been maximized, a step or means 70 receives the corresponding maximum performance index values, $v_i$, and corresponding scan parameter settings for each performance index priority. The maximum performance index values represent the best or maximum constraints to the corresponding performance indices which can be obtained.

Each of the achievable priorities and the corresponding scan parameters are stored in a look-up table 72, which look-up table may be addressed by the parameter estimator 14 of FIG. 2 to retreive the estimator parameter settings therefrom. The maximum achievable constraints for each priority is stored in a constraint look-up table 74. The constraint look-up table may be utilized in an off-line scan parameter setting selection system which is described below.

Figure 5:
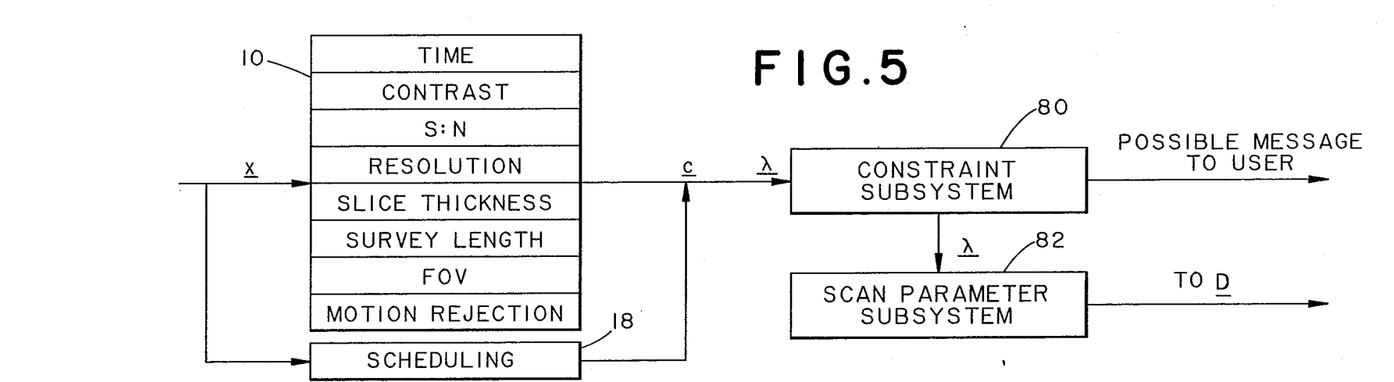
FIG. 5 illustrates a networked version of the integrated expert system.

FIG. 5 illustrates an alternate embodiment of the present invention. In the alternate embodiments like elements with the embodiment of FIGS. 1-4 are denoted for the same reference numeral. A performance indices means 10 is addressed with clinical descriptions to generate appropriate priorities and constraints. A constraints look-up table 80 such as the one generated at step or means 74 of FIG. 4 determines whether the constraints can, in fact, be met. If the constraints cannot be met, an appropriate message is sent to the operator. If the constraints can be met, then a look-up table 82 such as the one generated by step or means 72 of FIG. 4 selects the appropriate scan parameter settings for the scanner A. The selected scan parameter settings are printed out on the printer D as a part of the schedule selected by scheduling means or step 18 for each patient and each scan of each patient. The scan parameters may be implemented either automatically or manually by the operator when the scan is actually performed.

Figure 6:
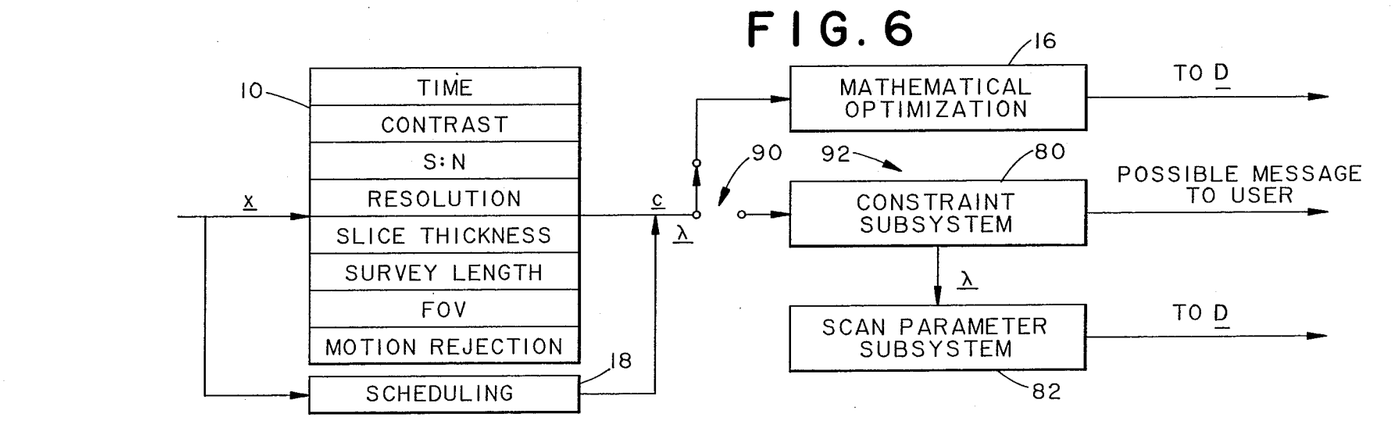
FIG. 6 illustrated a switched hybrid version of the integrated expert system; and, FIG. 7 illustrates a hybrid version of the integrated expert system with mathematical optimization and previously trained networked subsystems.

FIG. 6 illustrates a switched hybrid embodiment system. Priorities and constraints from a performance indices means 10 are switched by a switch 90 to either an on-line mathematical optimization expert system 16 or an off-line preprogrammed expert system 92. In particular, a constraint subsystem 80 determines whether the selected constraints can be met. If not, a message is provided to the user indicating an adjustment in the constraints is necessary. The constraint subsystem may be a look-up table or a probability based sub-system as discussed above. A scan parameter subsystem 82 selects the corresponding scan parameters. The scan parameters expert system 82 may be a preprogrammed look-up table that is programmed in accordance with Table 74 of FIG. 4.

Figure 7:
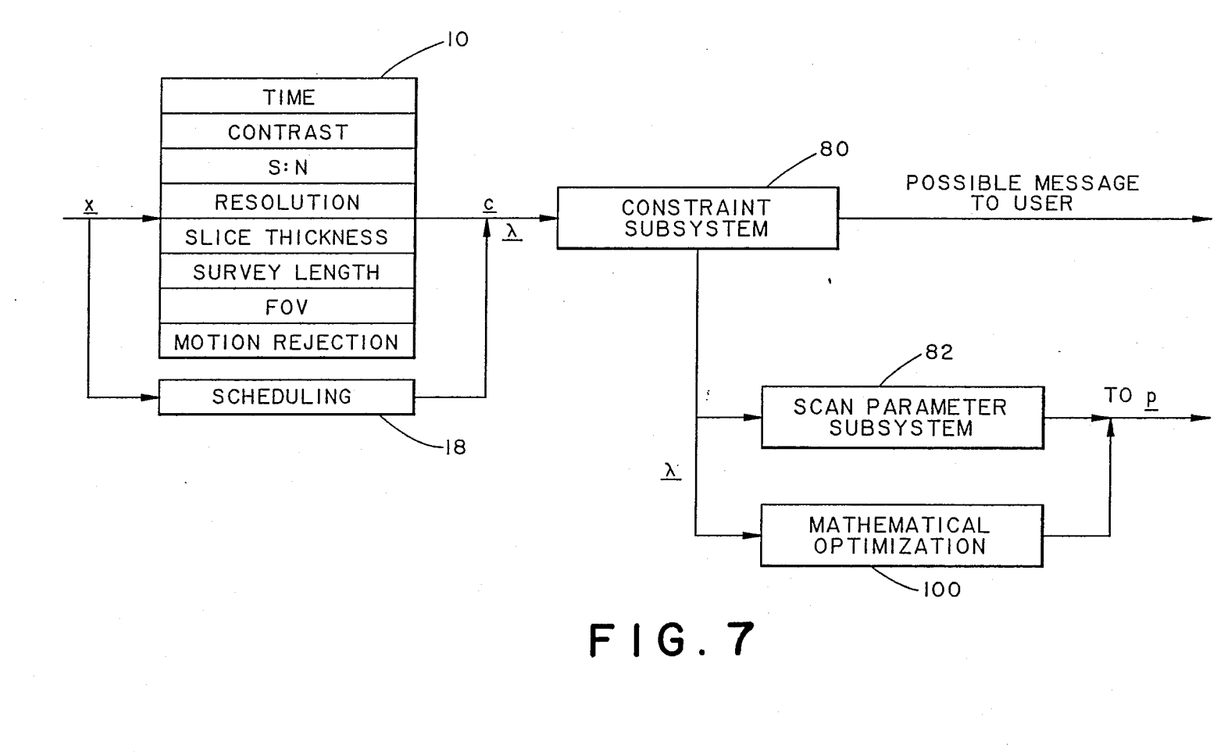

FIG. 7 illustrates another hybrid expert system which uses mathematical optimization and networked expert system. In particular, a constraint system 80 receives the priorities and constraints from the performance index means 10. If the constraints cannot be met, a message is sent to the operator directing that the constraints and priorities be altered. If the constraints can be met, a scan parameter subsystem 82 such as a look up table, is programmed to determine settings for a preselected partial set of the scan parameters. The remaining scan parameters are determined by an mathematical optimization subsystem 100 which functions analogously to the expert systems 16 of FIG. 3. In the preferred embodiment, the simpler variables are determined by the scan parameter system 82. The more complex and interrelated scan parameters, such as contrast, are mathematically optimized based on the constraints, priorities, and the previously selected scan parameter settings.

The invention has been described with reference to the preferred embodiment. Obviously, alterations and modifications will be apparent to those or ordinary skill in the art upon reading and understanding the preceding specification. It is intended that the invention be construed as including all such alterations and modifications in so far as they come within the scope of the appended claims or the equivalents thereof.

Having thus described the preferred embodiments, the invention is now claimed to be:

1. A medical imaging system comprising:
    non-invasive examination means for examining a subject and producing electrical signals indicative thereof, the examination means having a plurality of adjustable operating parameters;
    an image reconstructing means for reconstrucing an image from the electrical signals, the image being described by a plurality of performance indices which are related to the operating parameters by a preselected mathematical model, each performance index having a preselected idal value which ideal values are unattainable for all performance indices simultaneously, the image reconstruction means being operatively connected with the examination means to receive the electrical signals therefrom;
    a performance index means for calculating selected relative priorities for optimizing each performance index value from received clinical information on the subject and an intended diagnostic application for the image;
    an optimizing means for optimizing conformity of the performance index values predicted by the mathematical model and the ideal values in accordance with the relative priorities and providing an output of corresponding operating parameter adjustments, the optimizing means being operatively connected with the performance index means for receiving the priorities therefrom and with the examination means for supplying the operating parameter ajustments thereto.

2. A magnetic resonance imaging apparatus comprising:
    a magnetic resonance means for causing magnetic resonance in selected dipoles of a subject to be imaged and for receiving magnetic resonance signals from the resonating dipoles, the resonance apparatus having a plurality of adjustable scan parameters including scan sequence, sequence duration, and the like;
    an image reconstruction means for reconstructing and displaying a resultant image from the received magnetic resonance signals, the image reconstruction means being operatively connected with the resonance apparatus to receive the resonance signals therefrom; and,
    a scan parameter selection means for selectively setting for the adjustable scan parameters from input clinical information on the subject to be imaged and an intended application for the resultant image, the scan parameter selection means being operatively connected with the magnetic resonance means, whereby the image is reconstructed from resonance signals caused with appropriate scan parameters for the subject and intended use of the image.

3. The apparatus as set forth in claim 2 wherein the scan parameter selection means includes:
    an input means for receiving the clinical information;
    a first expert system for deriving constraints on values for each of a plurality of performance indices and a priority or weighting factor for each performance index from the clinical information, the first expert system being operativey connected with the input means; and,
    a second expert system for deriving the scan parameter settings from the constraints and priorities, the second expert system being operatively connected with the first expert system to receive the constraints and priorities therefrom.

4. The apparatus as set forth in claim 3 further including a manual override means for manually entering a portion of the performance indices constraints and priorities, the manual override means being operatively connected with the second expert system for supplying operator selected constraints and priorities thereto.

5. The apparatus as set forth in claim 3 wherein the performance indices and scan parameters are interrelated such that selecting each scan parameter setting affects a plurality of performance indices values, the second expert system including:
   a peformance funtional means for determining the value of a performance function which is determined by (i) a function of conformity with a preselected ideal performance index value within the constraint and (ii) the priority for each performance index; and,
   an optimizing means for determining whether the performance functional is optimized.

6. The apparatus as set forth in claim 5 wherein the second expert system further includes a means for interatively adjusting the scan parameter settings until the optimizing means determines that the performance functional is optimized.

7. The apparatus as set forth in claim 6 further including a parameter estimator system for estimating scan parameter settings from the performance index constraints and priorities from the first expert system, the parameter estimator means being operatively connected with the second expert system for providing the estimated scan parameter settings thereto such that the second expert system iteratively adjusts the scan parameter settings starting with the estimated settings to optimize the performance functional.

8. The apparatus as set forth in claim 3 further including a scheduling expert system for receiving subject data and deriving scheduling constraints and priorities, the scheduling means being operatively connected with the second expert system to supply the scheduling constraints and priorities thereto such that the second expert system derives a subject schedule from the received scheduling constraints and priorities.

9. An operating parameter selection system for medical diagnostic imaging equipment comprising:
   an input means for receiving intended application data;
   a first expert system for deriving constraints for values of each of a plurality of preselected image performance indices and a relative priority for each image performance index from the received intended application data, the first expert system being operatively connected with the input means;
   a second expert system for deriving operating parameter settings from the image performance index constraints and priorities, the image performance indices and the operating parameters being interrelated such that at least some of the image performance indices affect more than one operating parameter and at least one operating parameter is affected by several image performance indices, the second expert system being operatively connected with the first expert system to receive the image performance indices and priorities therefrom;
   means for generating a signal indicative of the operating parameter settings; and,
   means adapted for communicating the signal to the associated medical diagnostic imaging equipment.

10. The system as set forth in claim 9 wherein the medical diagnostic imaging equipment has a plurality of operating parameter settings, the medical imaging equipment being operatively connected with the second expert system for receiving the operating parameter settings therefrom; and having means for adjusting operation of the medical imaging equipment in accordance with received operating parameter settings.

11. The system as set forth in claim 9 wherein the medical diagnostic imaging equipment includes:
   a magnetic resonance apparatus which has a plurality of operating parameter settings, the magnetic resonance apparatus being operatively connected with the second expert system for receiving operating parameters settings therefrom; and
   means for adjusting the magnetic resonance apparatus in accordance with received operating parameter settings.

12. The system as set forth in claim 11 wherein the magnetic resonance apparatus is a spectrometer.

13. The system as set forth in claim 9 wherein the second expert system iteratively adjusts the operating parameter settings until the image performance indices are optimized.

14. The system as set forth in claim 13 further including an operating parameter estimating means for estimating operating parameter settings, the operating parameter estimating means being operatively connected with the first expert system to receive image performance index constraints and priorities therefrom and being operatively connected with the second expert system for supplying estimated operating parameter settings thereto to initiate the iterative adjusting process.

15. The system as set forth in claim 9 further including a scheduling expert system for deriving scheduling constraints and priorities from input scheduling consideration data, the scheduling expert system being operatively connected with the second expert system to supply the scheduling constraints and priorities thereto such that the second system derives a patient schedule therefrom.

16. The system as set forth in claim 9 wherein the second expert system includes:
   a look-up table means which is addressed by the constraints and priorities of a preselected subset of the image performance indices to retrieve corresponding operating parameter settings; and,
   a mathematical optimization system for receiving the constraints and priorities of other image performance indices from the first expert system and adjusting corresponding operating parameter settings until the values of the image performance indices with the highest priorities are preferentially optimized while the values of substantially all image performance indices are retained within the constraints.

17. A method of medical imaging comprising:
   selecting clinical data on a subject to be imaged and intended image diagnostic utility;
   in a first expert computer system, converting the clinical data into a plurality of image performance index constraint and priority values, the image performance index constraint and priority values and the clinical data being interrelated such that at least one of the image performance index constraint and priority values is affected by a plurality of the clinical data and such that at least one value of the clinical data affects a plurality of the image performance index constraint and priority values;

in a second expert computer system, deriving a plurality of operating parameter settings from the image performance index constraint and priority values, the image performance index constraints and priority values and the operating parameter settings being related such that at least one of the operating parameter settings is affected by a plurality of the image performance index constraint and priority values and at least one of the image performance index constraint and priority values affects a plurality of operating parameter settings;

scanning a subject to be imaged using the derived operating parameter settings.

18. The method as set forth in claim 17 wherein the step of deriving the operating parameter settings includes iteratively adjusting the operating parameter settings, each iterative adjustment altering the image performance index values, the iterative operating parameter setting adjustment being continued until the values of the image performance indices are adjusted for greater conformity to preselected values with greatest emphasis for conformity being given to the values of the image performance indices with the highest priority values.

19. The method as set forth in claim 18 further including the step of storing optimized operating parameter settings for a plurality of potential image performance index constraint and priority values and wherein in the iterative adjustment step, corresponding stored operating parameter settings are retrieved as a starting point for the iterative adjustment step.

20. The method as set forth in claim 18 wherein in the iterative adjustment step, only a portion of the operating parameter settings are iteratively adjusted and the remaining operating parameters are retrieved directly from a look-up table.

21. A method of operating parameter optimization for medical diagnostic imaging comprising:

receiving intended use data in a computer;

deriving in the computer constraints on values of each of a plurality of preselected image performance indices and a relative priority for each image performance index from the received data;

deriving in the computer operating parameter settings from the image performance index constraints and priorities;

generating a signal indicative of the operating parameter settings;

communicating the signal to an associated medical diagnostic imaging device; and, adjusting the associated medical diagnostic imaging device to operate with the derived operating parameter settings.

22. The method as set forth in claim 21 wherein the operating parameter setting deriving step includes:

adjusting the settings and determining image performance index values of the associated apparatus operating with the adjusted settings from a preselected mathematical model which relates operating parameter settings and image performance index values;

comparing each determined image performance index value with the corresponding constraints and with a corresponding preselected ideal value;

repeating the adjusting and comparing steps until conformity of the determined image performance index values with the preselected ideal values is maximized with conformity of higher priority image performance indices being weighted more heavily.

* * * * *